(12) United States Patent
Kotzer et al.

(10) Patent No.: US 9,637,770 B2
(45) Date of Patent: May 2, 2017

(54) METHODS AND DEVICES FOR HANDLING BIOFOULING

(75) Inventors: Eli Kotzer, Netanya (IL); Robert Armon, Givat Nesher (IL)

(73) Assignee: MEKOROT WATER COMPANY, LTD., Tel-Aviv (IL)

( * ) Notice: Subject to any disclaimer, the term of this patent is extended or adjusted under 35 U.S.C. 154(b) by 0 days.

(21) Appl. No.: 14/003,305

(22) PCT Filed: Mar. 7, 2012

(86) PCT No.: PCT/IL2012/050080
§ 371 (c)(1),
(2), (4) Date: Sep. 5, 2013

(87) PCT Pub. No.: WO2012/120517
PCT Pub. Date: Sep. 13, 2012

(65) Prior Publication Data
US 2013/0344533 A1  Dec. 26, 2013

Related U.S. Application Data

(60) Provisional application No. 61/449,887, filed on Mar. 7, 2011.

(51) Int. Cl.
*C12Q 1/04* (2006.01)
*B01D 61/12* (2006.01)
*B01D 65/08* (2006.01)

(52) U.S. Cl.
CPC ............ *C12Q 1/04* (2013.01); *B01D 61/12* (2013.01); *B01D 65/08* (2013.01); *B01D 2313/00* (2013.01); *B01D 2321/00* (2013.01); *C12Q 2304/24* (2013.01)

(58) Field of Classification Search
None
See application file for complete search history.

(56) References Cited

U.S. PATENT DOCUMENTS

2009/0064425 A1\* 3/2009 Scrivens et al. ............. 8/508

FOREIGN PATENT DOCUMENTS

| JP | 2-163098 A | 6/1990 |
|---|---|---|
| JP | 9-184835 A | 7/1997 |
| JP | 9-184837 A | 7/1997 |
| JP | 2001-299383 A | 10/2001 |
| JP | 2004-526152 A | 8/2004 |
| JP | 2004323797 A | 11/2004 |
| JP | 3813410 B2 | 8/2006 |
| JP | 2009-145087 A | 7/2009 |
| JP | 2010-43890 A | 2/2010 |
| JP | 2010-513935 A | 4/2010 |
| JP | 2010-154847 A | 7/2010 |
| WO | 00/24438 A1 | 5/2000 |

OTHER PUBLICATIONS

Iscan et al., Journal of Agricultural and Food Chemistry, 2002, vol. 50, No. 14 pp. 3943-3946.\*
Ergul et al., Chemistry, vol. 18, Iss. 3 (2009), pp. 36-48.\*
EMD Millipore Product Information, retrieved from the internet Feb. 19, 2015: http://www.thomassci.com/2D6DB8AC-50CC-4D93-AAAF-9207021DB0ED/_/74150ADF-9E78-4264-B43A-4ECCD84B87C3?q=Silica%20Gel.\*
Cybercolloids, Introduction to Agar-Properties, retrieved from the internet Dec. 4, 2015: www.cybercolloids.net/information/technical-articles/introduction-agar-properties.\*
Dictionary.com, Associate, retrieved from the internet, Dec. 7, 2015, pp. 1-7: http://dictionary.reference.com/browse/associate.\*
Maysoon et al., A Milk Basd Method fo Detecting Antimicrobial Substances Produced by Lactic Acid Bacteria, Journal of Dairy Science, vol. 78, No. 6, 1995, pp. 1219-1223.\*
Armon, et al., "Sol-gel applications in environmental biotechnology", Journal of Biotechnology, vol. 51, pp. 279-285, (1996).
Goldman, et al., "Inhibition of biofilm formation on UF membrane by use of specific bacteriophages", Journal of Membrane Science, vol. 342, pp. 145-152, (2009).
Armon, et al., A Quantitative and Qualitative Study of Biofilm Disinfection on Glass, Metal and PVC Surfaces by Chlorine, Bromine and Bromochloro-5,5 Dimethylhydantoin (BCDMH), Wat. Sci. Tech., vol. 38, No. 12, pp. 175-179, (1998).
Neugebauer, et al., "Antagonistic Action of *Lactobacillus delbrueckii* ssp. *lactis* RM2-5 Toward Spoilage Organisms in Cottage Cheese", J. Dairy Sci., vol. 88, pp. 1335-1341, (2005).
International Search Report (PCT/ISA/220 and PCT/ISA/210) for International Application No. PCT/IL2012/050080, six pages, mailed Jul. 27, 2012.
Turner, et al., "Use of Tetrazolium Dyes in an Agar Medium for Differentiation of *Streptococcus lactis* and *Streptococcus cremoris*", Journal of Dairy Science, vol. 46, pp. 380-385, (1963).
Hayashi, et al., "Simple and Rapid Cell Growth Assay Using Tetrazolium Violet Coloring Method for Screening of Organic Solvent Tolerant Bacteria", Journal of Bioscience and Bioengineering, vol. 96, No. 4, pp. 360-363, (2003).
Anonymous: "Polysulfone—Wikipedia, the free encyclopedia", Mar. 31, 2016 (Mar. 31, 2016), XP055261878.
Anonymous: "Polysulfone Microspec Corporation Advanced Medical Extrusions", Mar. 31, 2016.
Anonymous: "Polyimide—Wikipedia, the free encyclopedia", Mar. 31, 2016. XP055261885.
Anonymous: "Thermoset Polymers: Polyimide", Mar. 31, 2016. XP055261889, Retrieved from the Internet on May 17, 2016: http://www.thomasnet.com/articles/plastics-rubber/thermoset-polyimide.

\* cited by examiner

*Primary Examiner* — Thane Underdahl
*Assistant Examiner* — Yvonne Pyla
(74) *Attorney, Agent, or Firm* — Vorys, Sater, Seymour & Pease LLP

(57) ABSTRACT

Provided is a biosensor including a scaffold and a dye complex, the dye complex including a clay material associated with a dye material, where the dye complex is at least partially embedded in the scaffold. Also provided is a process for preparing the biosensor, an apparatus including the biosensor and methods for detecting viable microorganisms in an aqueous fluid test sample making use of the biosensor, for predicting biofouling in a fluid flowing system and for determining a concentration of disinfectant required to disinfect an aqueous fluid.

22 Claims, 4 Drawing Sheets

METHODS AND DEVICES FOR HANDLING BIOFOULING

FIELD OF THE INVENTION

The present invention generally relates to biofouling, and specifically to methods and devices for predicting and reducing biofouling in fluid systems, such as desalination systems.

BACKGROUND OF THE INVENTION

The problem of biofouling of membranes, pipes, cooling towers and other water-contacting surfaces is an ongoing problem in water-related processes and systems, and particularly in water desalination processes.

Development of biofouling on membrane surfaces presents one of the more serious problems in operating desalination plants based on reverse osmosis (RO) technology, especially for desalination of treated wastewater after secondary treatment.

The layer of biofouling on the membranes causes an increase in the input pressure, a decrease in product flow and an increase in the pressure drop on the surface of the membranes between the feed side and the concentration side. These changes cause a decrease in the production of the desalination facilities, an increase in energy consumption and a frequent need for chemical cleaning of the membranes in order to remove the biofouling layers.

The development of the biofouling results from adsorption and growth of microorganisms, found in the feed water, on the membrane surfaces.

Several methods are available for the prediction of biofouling, same are laboratory tests that include AOC (Assimilable Organic Carbon), BDOM (Biodegradable Dissolved Organic Matter) BOD (Biochemical Oxygen Demand), DOC (Dissolved Organic Carbon), TBC (Total Microorganisms Count), TOC (Total Organic Carbon). For field tests most of the measurements based on growing of biofilm on measuring surfaces. Several commercial biofilm identification kits are available, which detect presence of biofilm; the most common of these is the Biological Activity Reaction Test (BART) kit or the HydroBio Test kit.

Dyes for detecting microorganisms were also described. [Turner Nikki, W. E. Sandine, P. R. Elliker, and E. A. Day, "*Use of Tetrazolium Dyes in an Agar Medium for Differentiation of Streptococcus Lactis and Streptococcus Cremoris*", Journal of Dairy Science, 46:380-385 (1963); Hayashi Shuhei, Takeshi Kobayashi, and Hiroyuki Honda, "*Simple and rapid cell growth assay using tetrazolium violet coloring method for screening of organic solvent tolerant bacteria*", Journal of Bioscience and Bioengineering, 96(4):360-363 (2003)].

SUMMARY OF THE DISCLOSURE

The present disclosure provides, in accordance with one aspect, a biosensor comprising a scaffold and a dye complex, the dye complex comprises a clay material associated with a dye material and wherein the dye complex is at least partially embedded in the scaffold.

In yet a further aspect, the present disclosure provides a process for the preparation of a biosensor, the method comprises: (i) mixing a dye complex comprising a clay material and a dye material with a scaffold-forming material at a temperature at which the dye complex and the scaffold forming material are in an aqueous fluid mixture; (ii) adding to the fluid mixture a non-electrolytic reagent; and (iii) cooling the fluid mixture with the non-electrolytic reagent to a temperature at which the mixture solidifies; whereby a biosensor comprising the scaffold and the dye complex being at least partially embedded in the scaffold us formed.

In yet a further aspect, the present disclosure provides an apparatus comprising at least one fluid inlet and at least one fluid outlet, said fluid inlet and fluid outlet being in fluid communication; a biosensing chamber being positioned between the fluid inlet and the fluid outlet and comprising a biosensor comprising (i) a scaffold and (ii) a dye complex comprising a clay material and a dye material; wherein the dye complex is at least partially embedded in the scaffold.

In another aspect the present disclosure provides a method for detecting viable microorganism in an aqueous fluid test sample, comprising
(a) contacting the aqueous fluid test sample with a biosensor comprising (i) a scaffold and (ii) a dye complex comprising a clay material and a dye material, wherein the dye complex is at least partially embedded in the scaffold;
(b) detecting a signal intensity of the biosensor, the signal intensity being indicative of the presence of microorganism in the aqueous fluid test sample.

In yet another aspect, the present disclosure provides a method for predicting biofouling in a fluid flowing system, the method comprising:
(a) contacting an aqueous fluid sample from the aqueous fluid flowing system, with a biosensor comprising (i) a scaffold and (ii) a dye complex comprising a clay material and a dye material, the dye complex being at least partially embedded in the scaffold;
(b) detecting a signal intensity in the biosensor, the signal intensity being correlative to potential of the fluid flowing system to form bio-fouling.

In accordance with a further aspect, the present disclosure provides a method for determining a concentration of disinfectant required to disinfect an aqueous fluid, the method comprising:
(a) contacting one or more samples of the aqueous fluid with one or more different concentrations of a disinfectant;
(b) contacting each of the one or more sample containing the disinfectant with a biosensor comprising (i) a scaffold and (ii) a dye complex comprising a clay material and a dye material wherein the dye complex is at least partially embedded in the scaffold;
(c) for each of the one or more samples, detecting signal intensity of the biosensor;
(d) selecting a sample for which the signal intensity is between a range determined as being an effective treatment for said aqueous fluid or for said disinfectant; wherein the concentration of the disinfectant added to the selected sample is the concentration effective for disinfecting the aqueous fluid.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
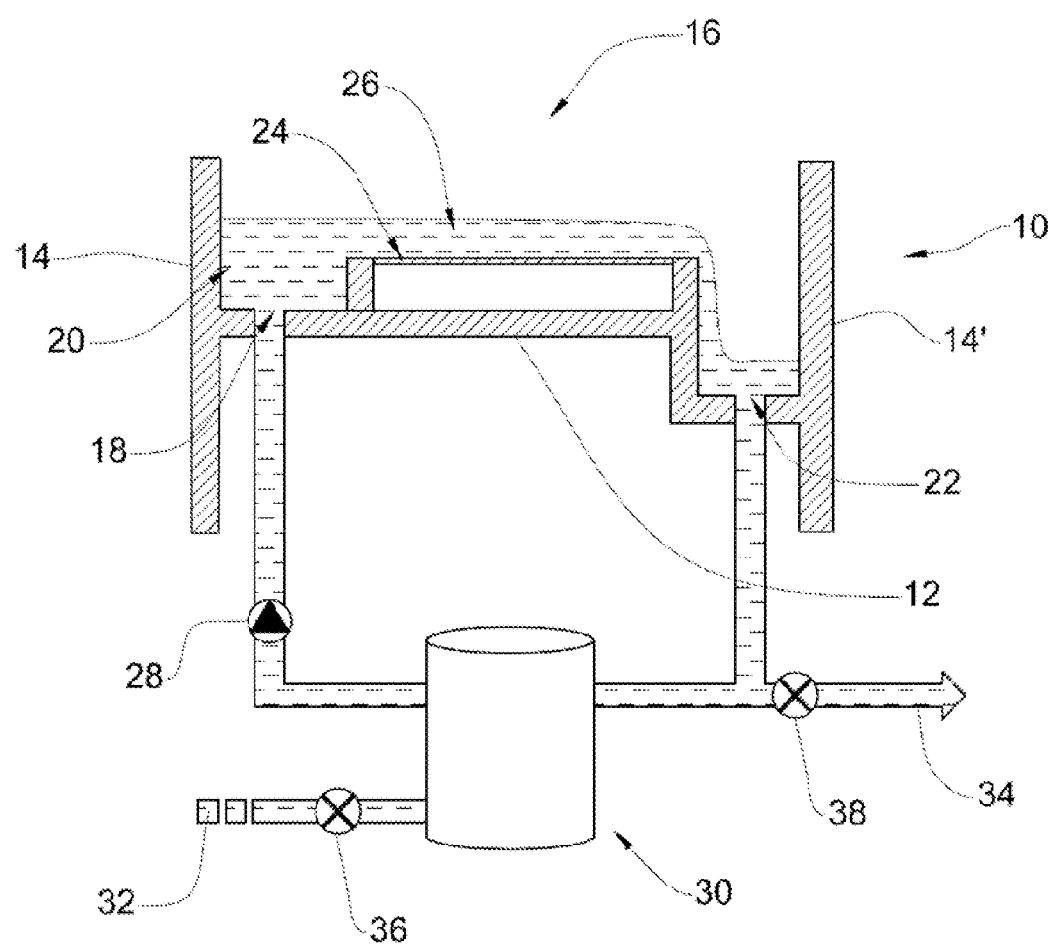
FIG. 1 provides a schematic cross section illustration of a biosensing apparatus (10) in accordance with an embodiment of the invention.

The present disclosure is based on the development of an immobilized biosensing material allowing the detection of even small amounts of microorganisms in flowing liquid. The biosensing material was thus incorporated into a fluid communication system to allow prediction of biofouling and thereby prevent clogging of membranes as a result of biofouling formation.

The present disclosure provides a reliable, quantitative and reproducible field, real-time, biosensor and apparatus containing same for determining potential for biofouling formation.

Moreover, as will be discussed hereinbelow, the biosensor allows correlation between its measurements and biofouling potential in input fluid (flowing fluid, e.g. flowing water), and to determine possible fluid treatment protocol, based on the results of the correlation.

Therefore, in accordance with a first aspect, the present disclosure provides a biosensor comprising a scaffold and a dye complex comprising a dye material and a clay material associated with the dye material; wherein the dye complex is at least partially embedded in the scaffold.

In accordance with a second aspect, the present disclosure provides a process for the preparation of a biosensor, the method comprises:

(a) mixing a dye complex comprising a clay material and a dye material with a scaffold-forming material at a temperature at which the dye complex and the scaffold forming material are in an aqueous fluid mixture;

(b) adding to the fluid mixture a non-electrolytic reagent; and (c) cooling the fluid mixture with the non-electrolytic reagent to a temperature at which the mixture solidifies;

whereby a biosensor is formed comprising a scaffold and the dye complex being at least partially embedded in the scaffold.

The "scaffold" is a matrix formed from any scaffold forming material. The scaffold forming material may be a natural, semi-synthetic or a synthetic scaffold forming material having a phase transition temperature from solid to liquid above 35° C., at times above 50° C. and even above 65° C. In some embodiments, the phase transition temperature is not more than 95° C. The scaffold is of a type to which microorganisms are capable to adhere, and the adhered microorganisms being capable of growing thereon. Further, the scaffold is characterized by pores/voids the dimensions of which manipulated in the presence of a chemical agent or physical conditions. For example, dehydration of a scaffold forming material may result in constriction of the scaffold's voids. Dehydration may be achieved by exposing scaffold forming material to alcohol.

Upon cooling, the scaffold forming material solidifies. In the context of the present disclosure, solidification includes transition into solid as well as semi- (quasi-) solid form.

In some embodiments, the scaffold forming material is a polymeric material. According to some embodiments, the polymer forming the scaffold may be selected from the group consisting of a polysaccharide, silicon-based polymers, polytetrafluoroethylene, polyethelene, polypropylene, polyethyleneterephthalate, polyurethane, polystyrene, polysulfone, polyester, polyhydroxyacids, polycarbonate, polyimide or polyamide.

In one embodiment, the scaffold forming material comprises one or more polysaccharides. A non-limiting list of polyseccharides includes agar, chitosan, cellulose, arabinoxylans, starch, glycogen and chitin.

In one embodiment, the scaffold is agar which is known to be produced from algae and composed of a mixture of two polysaccharides: agarose and agaropectin. While agar is well known in the art, Tables 1A and 1B provide some properties of Agar which may be used in accordance with the present disclsoure.

Tables 1A and 1B provide some agar properties and agar inorganic ingredients, respectively (obtained from http://www.bd.com/ds/technicalCenter/inserts/Agars.pdf).

TABLE 1A

| Agar properties (1.5% in water) | |
|---|---|
| Ash % | 3.6 |
| Clarity (NTU) | 4.3 |
| Loss on Drying (%) | 17.3 |
| pH | 6.5 |
| Gel Strength (g/cm2) | 600 |
| Gelation Point (° C.) | 35° C. |
| Melting Point (° C.) | 88° C. |

TABLE 1B

| Agar inorganic ingredients (1.5% in water) | |
|---|---|
| Element | % |
| Calcium | 0.179 |
| Chloride | 0.021 |
| Cobalt | <0.001 |
| Copper | <0.001 |
| Iron | 0.002 |
| Lead | <0.001 |
| Magnesium | 0.068 |
| Manganese | <0.001 |
| Nitrate | <0.005 |
| Phosphate | <0.005 |
| Potassium | 0.121 |
| Sodium | 0.837 |
| Sulfate | 1.778 |
| Sulfur | 0.841 |
| Tin | <0.001 |
| Zinc | <0.001 |

The "dye complex" is to be understood to encompass any physical association (bonding) between a dye material and a clay material, wherein the dye material forms non-covalent interaction with the clay material. Non-covalent interactions (non-covalent chemical bonding) may include, without being limited thereto ionic bonds, hydrogen bonds, van der Waals forces and hydrophobic interaction. The interaction between the dye material and the clay material is further discussed below.

The "dye material" is to be understood as encompassing any chemical compound that provides a detectable signal in the presence of microorganisms and in response thereto, e.g. as a result of microorganism metabolism. To this end, the chemical substance should be at least non-toxic to microorganisms and of a type that undergoes a change in the presence of metabolic products of microorganism (responsive to the presence of same).

In general, dye materials may be broadly divided into two groups:

(i) dye materials which provide a signal in response to the environment, for example in response to a change in pH (pH indicators) or in response to a reduction-oxidation reaction (redox indicators).

(ii) dye materials which provide a signal due to a change in their chemical structure. For example, a chemical change in the chemical formula or configuration (stereochemistry) in the compound due to an enzymatic activity (e.g. metabolic) of the microorganisms.

In accordance with the above, the dye material may be selected from a chromophore or fluorophore.

Dye materials were previously used to determine the presence of microorganisms in tested media introduced into 96 well plates. The present disclosure now makes use of dye material for detecting microorganisms in flowing or circulating fluids, e.g. flowing water, and not in standing fluids, as previously described. [Turner Nikki, et al. Journal of Dairy Science, 46:380-385 (1963); Hayashi Shuhei, et al. Journal of Bioscience and Bioengineering, 96(4):360-363 (2003)]

For example, the presence of coliforms in water may be identified using chlorophenol red β-d-galactopyranoside, which changes its color from yellow to red in the presence of β-d-galactosidase Toluene-decomposing microorganisms under anaerobic conditions in groundwater, may be identified through the use of trifluoro-m-cresol which changes its color to yellow when decomposes.

According to some embodiments, the dye material employed in accordance with the invention belongs to the family of tetrazolium compounds.

Tetrazolium compounds are mainly colorless or weakly colored and are reduced by dehydrogenases or reductases in a microorganism's electron transport chain to form chromophores, i.e. formazans as illustrated below:

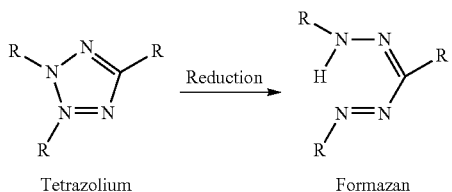

Tetrazolium        Formazan

Formazans have a variety of colors ranging from dark blue to deep red to orange, depending on the original chemical properties of the tetrazolium compound which are determined by the various organic groups bonded to the tetrazole ring (represented by the R moieties). The color change may be detected within a few hours in visible light or under ultraviolet radiation.

In general, tetrazolium compounds may be divided into subgroups, according to the site at which the tetrazolium compound reduction activity with respect to the microorganisms cell:

(i) Tetrazolium compounds which produce a formazan derivative that is soluble in water. Reduction of such tetrazolium compounds takes place outside the microorganism's cells.

(ii) Tetrazolium compounds which produce a formazan derivative that is not soluble in water. Such tetrazolium compounds, especially the monotetrazolium group, penetrate the cell envelope and thus the reduction reaction takes place within the cell.

The tetrazolium compounds may be selected from the non-limiting group consisting of 2-(4-iodophenyl)-3-(4-nitrophenyl)-5-phenyl tetrazolium chloride (INT), 2-(4,5-dimethylthiazolyl)-3,5-diphenyl-2H-tetrazolium bromide (MTT), sodium 2,3-bis-(2-methoxy-4-nitro-5-sulfophenyl)-5-[(phenylamino)-carbonyl]-2H-tetrazolium-inner salt (XTT), 5-[3-(carboxymethoxy)phenyl]-3-(4,5-dimethyl-2-thiazolyl)-2-(4-sulfophenyl)-2H-tetrazolium inner salt (MTS), 2,3,5-Triphenyl-2H-tetrazolium chloride (TTC), sodium 5-(2,4-disulfophenyl)-2-(4-iodophenyl)-3-(4-nitrophenyl)-2H-tetrazolium inner salt (WST-1), 2,3,5-triphenyl-2H-tetrazolium chloride (red tetrazolium), 2,5-diphenyl-3-[alpha-naphthyl]-1-tetrazolium chloride (tetrazolium violet), 3,3'-(4,4'-biphenylene)bis(2,5-diphenyl-2H-tetrazolium chloride (neotetrazolium chloride), 3,3'-(3,3'-dimethoxy-4-4'-biphenylene)bis(2,5-diphenyl-2H-tetrazolium chloride (blue tetrazolium chloride), 3,3'-(3,3'-dimethoxy-4,4'-biphenylene)bis[2-(4-nitrophenyl)-5-phenyl-2H-tetrazolium chloride](nitroblue tetrazolium), or 3,3'-(3,3'-dimethoxy-4-4' biphenylene)bis[2,5-bis(4-nitrophenyl)-2H-tetrazolium chloride](tetranitroblue tetrazolium).

In a preferred embodiment, the dye material is of the type that is metabolized within the microorganism. This ensures that once the biosensor is brought into contact with flowing fluid, and the signal is created, the signal is not washed off the biosensor.

According to this embodiment, several tetrazolium compounds may be used, preferably monotetrazolium compounds.

Table 2 provides examples of specific monotetrazolium compounds which enter the cells to undergo a reduction reaction whereby a color is created.

TABLE 2

| monotetrazolium compounds | |
|---|---|
| Compound name | Molecular Weight (g/mole) |
| Triphenyltetrazolium chloride | 334.8 |
| Tetrazolium red | 348.5 |
| Tetrazolium violet ($C_{23}H_{17}ClN_4$) | 384.84 |

(Source: Graham D. Horace, 1967)

According to one embodiment, the tetrazolium compound is the tetrazolium violet (also known as 2,5-diphenyl-3-[alpha-naphthyl]-1-tetrazolium chloride).

In order to ensure entrapment of the dye material, a complex is formed with a clay material, acting as the dye anchor. The interaction (association) between the dye material and the clay material is non-covalent as discussed above.

In one embodiment, the interaction is based on the ionic interaction between positively charged dye material to the negatively charged clay material, resulting in a high molecular weight dye complex.

The "clay material" is to be understood as referring to any aluminum silicate composed primarily of grained minerals.

In one embodiment, the clay material comprises clay minerals. Clay minerals are hydrous aluminum phyllosilicates comprising variable amounts of iron, magnesium, alkali metals, alkaline earths and other cations.

Without being limited thereto, the clay mineral may be selected from the group consisting of Kaolin, Smectite, Illitem Chlorite, Sepiolite and Attapulgite.

In a preferred embodiment, the clay mineral is Kaolin. Kaolin is a white powdery substance comprising mostly the mineral kaolinite as well as other minerals such as dickite, halloysite and nacrite. Kaolin is well known in the art and is commercially available in various forms.

Kaolin as well as other clay minerals may be referred as "cation exchange" as clay materials usually comprise a negative charge on their surface and therefore are capable of adsorbing and holding positively charged species.

Without being bound by theory, the association between the dye materials to the clay material involves interaction between the positively charged dye material being adsorbed on the surface of the ionic clay material thereby forming the dye complex.

An advantage of using kaoline as the clay material resides in its natural white color, serving as a background color to enable a clear detection of the color change on the surface of the biosensor.

In the non-limiting example of the present invention, the amount of dye material that remained exposed on a surface of the scaffold having a surface area of 70 cm$^2$ was sufficient to allow detection of at least 40 CFU/ml microorganism (at TOC at least 1.2 mg/l).

According to some embodiments, the dye complex has a molecular weight in the range of 300 g/mole to 1500 g/mole, preferably in the range of 500 g/mole to 1300 g/mole, more preferably in the range of 700 g/mole to 1300 g/mole.

The entrapment or embedment, which is a physical (mechanical) entrapment of the dye complex in the scaffold may be achieved by exposing the scaffold forming material to a chemical agent such as a non-electrolytic reagent that results in the constriction of the scaffold forming material. The non-electrolytic reagent may be understood as denotes any chemical substance that does not exist in an ionic form in an aqueous solution.

Constriction may be achieved by dehydration (fully or partially) of the scaffold forming material in the presence of the dye complex, as will be further discussed below. As a result, the dye complex is at least partially embedded or entrapped in the scaffold. In this context, it is to be understood that "at least partially embedded in the scaffold" means that a portion of the dye material that is responsive to the presence of microorganisms in the fluid is exposed out of the scaffold, but yet, the dye complex is stably entrapped in the scaffold.

According to one embodiment, the embedment of the dye complex in the scaffold is provided by the exposure of the scaffold forming material to an alkanol. Therefore, in accordance with some embodiments of the invention, the biosensor comprises an alkanol.

The "alkanol" in the context of the invention denotes a saturated or non-saturated, straight or branched, aliphatic or aromatic hydroxyl containing carbohydrate. In some embodiments, the alkanol is an alcohol, e.g. a $C_1$-$C_{20}$ alcohol. This may include, without being limited thereto, methyl alcohol (methanol), ethyl alcohol (ethanol) tert-butyl alcohol, n-propyl alcohol, iso-propyl alcohol (sec-propyl alcohol), n-butyl alcohol, iso-butyl alcohol (sec-butyl alcohol).

In a preferred embodiment, the alcohol is ethanol.

According to the present invention, and without being bound by theory, it appears that the non-electrolytic reagent, such as an alkanol added to the scaffold and the dye complex, constricts the scaffold's pores and thus physically holds the dye complex and prevents the diffusion of the dye complex from the polymeric scaffold, e.g. in the presence of flowing fluid.

The non-electrolytic reagent is added to the mixture of the scaffold forming material and the dye complex material when in fluid form. To this end, the mixture of the components, namely, the scaffold forming material and the dye complex material is heated. In some embodiments, heating is to a temperature between 35° C. and 95° C., at times between 55° C. and 85° C. further at times, to a temperature in the range of 45° C.-85° C. or even 65° C. to 85° C. Then, a predetermined amount of the non-electrolytic reagent is added, the amount being in correlation with the level of constriction desired.

In some embodiments, the dye material and the clay material are mixed at a pH in the range of pH 4 to pH 6. In one particular embodiment; the mixing is at a pH of 4.5±0.5.

The thus formed homogenous mixture is then cooled to a temperature at which the mixture forms into a solid or semi-solid structure. In some embodiments, the temperature may be between 10° C. and 35° C., preferably between 20° C. and 30° C., and at times, between 20° C. and 25° C. In some embodiments, the scaffold-forming material is added in excess to the dye material. In one embodiment, the mixture is at a stoichiometric ratio of 2:1, at times 3:1 and even 4:1 between the scaffold forming material and the dye complex.

The biosensor in a solid or semi-solid may be provided in various forms. In one embodiment, dye complex embedded in the scaffold is provided as a laminate or layer on a plate. To this end, the fluid mixture may be casted into a template, such as a plate, covering the surface of the plate. The biosensor in the form of a laminate may be defined to have an upper surface and a bottom surface, with the dye material being exposed at least at the upper surface of the laminate.

The plate may be for example a microtiter plate (also known as microplate or microwell plate) prepared from a material selected from polystyrene, polypropylene, polycarbonate or cyclo-olefins. The microplate may have any number of wells. Commercially available plates comprise 6, 12, 24, 48, 96, 384 or even 1536 sample wells.

According to some other embodiments, the biosensor is in the form of particulate matter with the dye material being exposed at the outer surface of the particulate matter. The particulates may be obtained using well known spraying techniques or any other technique known to form beads.

The particulate biosensing material may then be suspended in a suitable buffer, in a container or housed in a column. When in particulate form, the diameter may vary, and in some embodiments, the size distribution of the particulate matter may be in the range of 0.01 micrometer to 10 micrometer. The particulates may be uniform in size or varying in size.

The biosensor may be disposable, for single use, may be re-used, for multiple testing. When used for more than once, it is purged between uses. Purging may be achieved by replacing the dye complex with new dye complex.

In the process for the preparation of the biosensor, it was found that the ability of the scaffold to trap a material within its pores is dependent on the polymer's pore size and that the size of the pores may be adjusted using higher than conventional (higher than recommended by manufacturer) concentration of the scaffold forming material. Reduced pore size, reduces the diffusion coefficient (outflow) of dye complex trapped within the scaffold.

Thus, for example, while in conventional growing mediums agar is used in a concentration of 1.8% in distilled water (which is the concentration recommended by Agar manufacturers), the inventors have found that in order to obtain an optimal entrapment of the dye complex in agar (optimal in the sense that the dye complex is not released from the biosensor once the fluid flows over the biosensor) the agar concentration in the fluid mixture should be increased by at least by two fold, at times 3 fold and even 4 fold increase, and in the specific examples was increased to 7.2%.

In one particular embodiment, the biosensor comprises a dye complex of kaoline and tetrazolium violet embedded in agar (the scaffold).

It is noted that agar is a gel at room temperature and remains solid at a temperature as high as 65° C. Agar melts at approximately 85° C., and then solidifies at a temperature under about 45° C., specifically at a temperature range of 32° C. to 40° C.

In line with this embodiment, the biosensor is prepared by a process comprising:
(a) mixing a dye complex comprising Kaoline and tetrazolium violet with agar at a temperature in the range of 65° C. to 85° C. to form a fluid mixture that retains the dye complex and the agar in aqueous fluid form;
(b) adding to the fluid mixture ethanol; and
(c) cooling the fluid mixture with ethanol to a temperature in the range of 20° C.-25° C.;
whereby a biosensor is formed comprising the dye complex being at least partially embedded in agar.

Also provided by the present disclosure is an apparatus comprising:
at least one fluid inlet and at least one fluid outlet being in fluid communication;
a biosensing chamber being positioned between the fluid inlet and the fluid outlet and comprising a biosensor comprising:
(i) a scaffold;
(ii) a dye complex comprising a clay material associated with a dye material;
wherein the dye complex being at least partially embedded in the scaffold.

A cross section illustration of a biosensing apparatus according to an embodiment of the invention is provided in FIG. 1.

Accordingly, a biosensing apparatus (10) comprises a base (12) and sidewalls (14) and (14'), a biosensing chamber (16), a fluid inlet (18) in the base proximal to one sidewall (14) for delivering fluid into the a damping basin (20) within biosensing chamber (16) and an outlet (22) proximal to the other sidewall (14') for expelling fluid out of biosensing chamber (16).

The biosensing chamber (16) comprise a biosensor (24) comprising a scaffold; and a dye complex comprising a clay material associated with a dye material; wherein the dye complex is at least partially embedded in the scaffold.

The biosensing chamber (16) may be constructed to carry one (as shown in FIG. 1) or an array of biosensors (not shown). The one or more biosensors may be aligned one next to the other and/or stacked one on top of the other in a manner allowing fluid to flow therebetween.

The damping basin (20) which at times may be referred to as a silencing basin, is used to quiet the fluid entering the biosensing chamber (16), i.e. reduce if not eliminate oscillations of fluid entering into the biosensing chamber (16) and to form a thin and quiet laminar flow (26) of liquid over the biosensor (24). Oscillation may occur as a result of the strokes of a pump (not shown) for withdrawing fluid into the biosensing apparatus.

The dimensions of a damping basin (20) is calculated so that the oscillations of fluid entering via inlet (18) are minimal and a constant laminar flow over the biosensor is formed.

For maintaining a laminar flow over the biosensor (24), it was necessary to calculate the conditions for obtaining a Reynolds number ($R_e$) below 2,000, even below 1,000 and at times even preferably between 300 and 800 (a Reynolds number above 2,000 correlates with turbulent flow). Reynolds number is calculated according to the equation:

$$R_e = \frac{Q_c \times L}{v \times A}$$

Where Qc is the volumetric flow rate (cm$^3$/s); L is the hydraulic radius of the conduit through which the fluid flows (cm); A is the flow cross-sectional area (cm$^2$); v is the kinematic viscosity (cm$^2$/s).

In this connection, it is noted that a flow through a straight conduit, a Reynolds number of less than 2000 is generally considered to be of a laminar type, wherein Reynolds numbers over 2000 indicates turbulent flow.

A laminar flow, in the context of the present disclosure means the formation of a layer of flowing fluid over the biosensor, with essentially even depth over the biosensor, the depth being between 0.5 mm-10 mm, even between 1 mm-5 mm and even 1 mm-3 mm.

Accordingly, for a damping chamber having a volume of 92.16 cm$^3$ (height 1.8 cm, length 4.0 cm and width 12.8 cm); and a laminar flow characterized by of depth of fluid over the biosensor of about 0.3 cm, a Reynolds number of 718 was obtained.

The apparatus inlet (18) and the apparatus outlet (22) are in a fluid communication. Specifically, the inlet (18) may transfer tested fluid into the biosensing chamber (16) for reacting with the biosensor (24) and the outlet (22) may transfer the tested fluid from the biosensing chamber (16) to a waste collector (not shown) or re-circulate the fluid into the inlet (18).

In some embodiments, the apparatus may comprise a pump (28) which may facilitate fluid flow within the apparatus or may be used for re-circulating fluid from outlet (22) to inlet (18) ("circulation pump").

The apparatus may also comprise a fluid reservoir (30) for holding fluid prior to introduction and analyzing in the biosensing chamber (16). The reservoir (30) receives fluid from a fluid source via fluid inlet line (32) and discharges fluid via fluid discharge line (34). The control of incoming and outgoing fluid via fluid inlet line (32) and fluid discharge line (34) may be controlled by valves (36) and (38), respectively.

In some embodiments, the apparatus may be part of a biosensing system, comprising one or more of the following units:

a temperature control unit for controlling the temperature of within at least the biosensing chamber, e.g. for supporting growth of microorganisms a signal detection unit. The signal detection unit may comprise a microscope equipped with color detector or UV detector or the like, which is used according to manufacturer's instructions.

scanner for scanning images of the one or more biosensors, e.g. optical scanning of the color.

processing unit for receiving input data from the detector or the scanner and outputting parameters indicative of the signal intensity of the biosensor. The processing unit may be part of a end-user module, such as a computer carrying a database of various biosensors, and biofouling indexes of various fluids.

Control unit for controlling the operation of the biosensing apparatus, including flow rate, temperature, etc. The control unit may be equipped with an alarm system for notifying a biofouling level above a predetermined threshold, for notifying a malfunction etc.

The apparatus according to the present invention may be operated automatically. When using an alarm system, direct intervention of a human operator may be minimized.

The control unit may be operated by a microprocessor and may be software controlled.

The present disclosure also provides a method for detecting viable microorganism in an fluid test sample, comprising
(a) contacting the aqueous fluid test sample with a biosensor as defined herein;
(b) detecting a signal intensity of the biosensor the signal intensity being indicative of the presence of viable microorganism in the fluid test sample.

In some embodiments, the fluid is an aqueous fluid, such as water. Water may be natural sweat water (e.g. from springs, lacks, ponds, rivers etc.) or natural salt water, e.g. seawater, or treated water, e.g. purified water, desalinated water, water in the process of desalination, etc., or wastewater.

The "contacting" is to an extent that a laminar flow of the aqueous fluid over the biosensor is provided, so as to ensure an intimate contact of the aqueous fluid and the dye complex.

As described above, the signal in the biosensor is a result of a formation of metabolic products of microorganism which thus depends on the presence of viable microorganism in the fluid circulating in a laminar flow over the biosensor.

As exemplified hereinbelow, a change in signal (color) appears on the surface of the biosensor only when there fluid flowing over the biosensor contained a combination of microorganisms and suitable nutrients. If one of these elements was missing or removed from the circulating fluid, no signal appeared as compared to the control (e.g. to circulating saline). In other words, growth of microorganisms on the biosensor, i.e. biofouling, would be solely attributed to metabolic activity in the presence of the food materials originally existing in the tested fluid.

In some embodiments, the tested fluid is water treated in a destination plant, e.g. water at any stage of RO filtration. To this end, it is desired to make use of the biosensor disclosed herein for predicting bio-fouling in a fluid flowing system, such as RO systems in desalination plants.

Accordingly, there is provided a method comprising:
(a) contacting an aqueous fluid sample from the aqueous fluid flowing system, with a biosensor as defined herein,
(b) detecting signal intensity in the biosensor (the signal being produced in response to metabolic products of microorganism if present in the sample), the signal intensity being correlative to potential of the fluid flowing system to form bio-fouling.

In the context of this method it is to be understood that a potential of a fluid means the probability due to the presence of microorganisms in the fluid that are capable of adhering to the biosensor, even if no bio-fouling has already occurred.

In line with the above method, it has been found that there is a linear positive correlation between the signal intensity on the biosensor and the fluid, e.g. water quality as measured by biofilm volume (biovolume) grown on, for example, RO membranes in desalination facilities.

In accordance with another aspect, the present disclosure provides a method for determining a concentration of disinfectant required to disinfect an aqueous fluid, the method comprising:
(a) contacting one or more samples of the aqueous fluid with one or more different concentrations of a disinfectant;
(b) contacting each of the one or more sample containing the disinfectant with a biosensor as defined herein;
(c) for each of the one or more samples, detecting signal intensity of the biosensor;
(d) selecting a sample for which the signal intensity is between a range determined as being an effective treatment for said aqueous fluid or for said disinfectant;
wherein the concentration of the disinfectant added to the selected sample is the concentration required for disinfecting the aqueous fluid.

In general, urban wastewater treated at purification plant contain a concentration of ammonia ($NH_3$) at values which vary between approximately 2-10 mg/L. When a disinfectant such as for example sodium hypochlorite (NaOCl) is added to this water, the chlorine bonds to the ammonia and chloramines ($NCl_3$, $NHCl_2$, $NH_2Cl$) are created.

In accordance with this aspect, the disinfectant may be any conventional agent for treating water.

Chlorine is the most widely used chemical disinfectant for use in water treatment and is marketed in many forms. The chlorine added to the water reacts with organic and inorganic material as well as with microorganisms. The amount of chlorine that is consumed by the treated water is called the "chlorine demand". The amount of chlorine remaining in the water after the chlorine demand has been satisfied is called "residual chlorine".

The conventional chlorine-based water treatment compounds include elemental chlorine (employed as chlorine gas), sodium hypochlorite, calcium hypochlorite, Sodium dichlor, Sodium dichloro-isocyanurate (NaDCC), sodium dichloroisocyanurate dihydrate ($NaDCC.2H_2O$), potassium dichloroisocyanurate (KDCC), trichloroisocyanuric acid (TCCA), chloramines, chlorine dioxide, sodium chlorite, sodium chlorate, potassium chlorate, hydrogen peroxide, ozone and mixtures thereof, The disinfectant may also include silver, copper, bromine compounds, periodic acid, a photocatalyst and combinations of same.

In one embodiment, the disinfectant is sodium hypochlorite.

To prepare water treating solutions, the solid chemical disinfectants are preliminarily dissolved in a separate vessel and the resulting mixture constituting the water treating solution is then taken out with suitable dosing pumps and fed into water to be treated.

It is important to note in this connection that reverse osmosis membranes are resistant to chloramines but are not resistant to chlorine, which oxidizes the surface of the membranes and causes a decrease in product flow and increase of input pressure. Therefore, it is very important to reduce the injection dose of the sodium hypochlorite, in order to prevent free chlorine from remaining in the input water and thereby possibly harming the membranes.

DETAILED DESCRIPTION ON SOME NON-LIMITING EXAMPLES

Materials

The following materials were used in the following examples

| Material | Source |
| --- | --- |
| Agar Bacto | Difco, USA |
| Tetrazolium violet | Sigma-Aldrich, Austria |
| Kaolin (china clay powder) | Spectrum, USA |
| HCl solution (0.1M) | Frutarom, Israel |
| Ethanol (EtOH, 96%), | Biolab, Israel |
| Nutrient Broth | Difco, France |
| Hypochlorite | Amgal, Israel |
| Total chlorine test instrument | Hach Lange, Germany |

System

A schematic illustration of a biosensing apparatus is provided in FIG. 1.

General

Prior to each experiment, the apparatus was disinfected with chlorine solution, and rinsed several times with distilled water to remove remaining traces on the chlorine.

Example 1

Biosensor Development and Testing

Sampling Site and Water Quality:

Water samples for the following non-limiting examples were obtained from the Shafdan purification plant (Shafdan, Israel), unless otherwise stated. The Shafdan purification plant is responsible for the purification of wastewater from cities in the Dan region, in Israel, and operates a water desalination facility comprising:

A pre-filter of 130 micron.

An ultrafiltertration (UF) pretreatment system comprising pores membranes of 0.02 micron.

A reverse osmosis (RO) system comprising three desalination stages (each stage desalinates brine of the previous step), with a recovery ratio of 90%.

Water parameters at different sampling times and locations ("Sampling Point") were determined by standard protocols conducted by AminoLab, Israel and are summarized in Table 3.

Total Organic Carbon (TOC) was determined by standard method 5310B High temperature combustion method.

Total Bacteria Count (TBC) was determined by Colony forming Unit method (CFU/ml)

Biochemical Oxygen Demand (BOD) was determined by standard method 5210B-5 Day BOD test Conductivity was determined by multi-parameter analyzer Consort C532, Belgium.

TABLE 3

Water quality at Sampling Points of the Shafdan*

| Sampling Point | Description | TOC (mg/l) | TBC (CFU/ml) | BOD (mg/l) | Conductivity (µmho) |
| --- | --- | --- | --- | --- | --- |
| 1 | Raw water after 130 micro screening | 9.0-12.1 | $10^5$-$10^6$ | 35 | 1,600-1,850 |
| 2 | Treated water after UF pretreatment | 8.0-11.5 | $3 \times 10^2$-$10^3$ | >5 | 1,600-1,850 |
| 3 | Feed water to RO stage I | 8.0-14.2 | $3 \times 10^2$-$10^3$ | >6 | 1,600-1,850 |
| 4 | Feed water to RO stage II | 23-39 | $6 \times 10^2$-$10^4$ | 14.5-25 | 3,900-4,700 |
| 5 | Feed water to RO stage III | 38.1-68.5 | $10^3$-$10^5$ | 24-103 | 5,800-6,740 |
| 6 | RO concentrate outlet | 80-115 | $6 \times 10^3$-$10^5$ | 50 | 12,000-14,000 |

*Range in parameters is due to changes in water quality throughout the measuring period Preparation of Biosensing Material:

Tetrazolium violet (0.15 mg) was dissolved in 30 ml DDW (to obtain stock solution concentration of 0.5%) while vortexing (i.e. mixing in a vortex). The solution was then sterilized by filtering through 0.45µ filter paper. The filtered solution was kept at a temperature of 4° C. in a closed test tube wrapped in aluminum foil.

Kaolin (1.5 gram) was dissolved in 60 ml distilled water to obtain a kaolin solution, at a concentration of 2.5% and the pH was adjusted to about pH of 4.5 using HCl 0.1M. The kaoline solution was sterilized in an autoclave at 120° C. for 17 minutes and allowed to cool at room temperature. Then, 3 ml of Tetrrazolium Violet stock solution was added to obtain concentration of 0.025%. The solution was stirred for 24 hours in an Erlenmeyer flask, which was wrapped in aluminum foil to keep the light out.

Agar (21.6 gram) was dissolved in 240 ml distilled water and the solution was mixed on a magnetic stirrer for 5 minutes, at room temperature, to obtain an agar solution at a concentration of 9.0%. The agar solution was sterilized in an autoclave at 120° C. for 17 minutes then the agar solution was allowed to cool to about 65° C. The 60 ml kaolin-tetrazolium violet solution was then added to the agar solution, such that the agar solution was diluted with the kaolin-tetrazolium violet solution at a ratio of 1:5 (4 parts agar solution and 1 part kaolin solution), to obtain a final concentration of 7.2% agar, 0.5% kaolin and 0.005% tetrazolium violet.

After mixing the two solutions for 10 minutes at a constant temperature of 65° C. (the constant temperature obtained using hot water bath) a homogeneous solution was obtained, and then 3 ml of ethanol (EtOH) was added to the homogeneous solution, while mixing, until reaching an ethanol concentration of 1% in the solution. This final solution is referred in the following examples as the biosensing medium.

The biosensing medium, at a temperature of 65° C. was poured into a 96-wells plate. The plates were immediately covered with aluminum foil while solidification took place, to prevent exposure to light.

Preliminary Assessment Color Detection:

A 96-wells plate was placed in a large container, with weights on the sides of the plate to prevent it from flowing. The plate was covered with a solution of water obtained from Sampling Point 1 up to a height of 1 cm above the plate's top surface (to completely cover the plate).

For control—two Petri dishes were used: one with sterile distilled water and the other with the tested water.

The plate and the two dishes were wrapped in aluminum foil and were placed in an incubator at a temperature of 35° C.

The 96 wells plate was photographed after 48 hours and after 72 hours. The purple color was detected on the plate already after 24 hours and was more intense after 72 hours, indicating that the intensity of the color is affected by the increased presence of the microorganisms. The control dishes (with saline only) were photographed after 72 hours.

In all Experiments, the following conditions were maintained:
 a. Throughout all of the experiments no nutrients were added and the growth of any microorganisms resulted from nutrients in the various liquids used.
 b. Before operation, disinfection was performed using of a chlorine solution which was circulated in the biosensor for two hours, after which the biosensor was rinsed several times with distilled water to remove remaining traces on the disinfectant.
 c. Control samples included identical number of wells with: (i) sterile solution, or (ii) water sampled from Sampling Point 1; (iii) water sampled from Sampling Point 1, from which the microorganisms were filtered out; and (iv) saline solution with microorganisms that were filtered from the water from Sampling Point 1.
 d. The biosensor was performed in the dark, as much as possible, in order to prevent damage to the fluorescent materials trapped in the agar layers.

Validation Experiments:
Experiments for Determining the Biosensor Activity and Sensitivity:

A. Firstly, the growth of microorganisms in the plates, in incubator conditions, was verified. To this end, either sterile saline or water from Sample Point 1 were each placed on a Petri dish and held in the incubator.

B. Then, sample test experiments were conducted for confirm the appearance or lack of appearance of a violet color in different samples as specified in Table 4, at different temperatures on the biosensing material within the 96-well plate. Each sample was circulated in the biosensor apparatus as described herein (see FIG. 1 as well). The Experiments were conducted in batches, each batch numbered as sample number/batch number. The time of circulation was 48, 72 or 96 hours, and during circulation, images of the plates were taken. In addition, for all samples the fluid flow in the apparatus was 90 ml/min and the volume of a tested sample was 2 L. The tested samples were circulated within the apparatus where the biosensing chamber carried a 96 well plate, each well containing the biosensing material.

TABLE 4

The tested samples and conditions for each experiment

| Batch No. | Tested sample | Hours[1] | Temp. (° C.) |
|---|---|---|---|
| 1/1 | Saline containing extracted microorganisms | 72 | 35 |
| 2/1 | Sample from Sampling Point 1 however diluted 1:1 with sterile saline | 72 | 35 |
| 3/1 | Sample from Sampling Point 1 | 72 | 35 |
| 1/2 | Sample from Sampling Point No. 1 mixed with 50 ml 1.8% Nutrient Broth; | 96 | 35 |
| 2/2 | Sample from Sampling Point 1 | 96 | 35 |
| 3/2 | Sample from Sampling Point 1 | 96 | 24 |
| 1/3 | saline containing extracted microorganisms | 48 | 35 |
| 2/3 | Sample from Sampling Point No. 1, from which any existing microorganisms was filtered out | 48 | 35 |
| 3/3 | Sample from Sampling Point 1 | 48 | 35 |
| 1/4 | Sample from Sampling Point No. 1 mixed with 15 ml 1.8% Nutrient Broth | 72 | 35 |
| 2/4 | Sample from Sampling Point No. 1, from which any existing microorganisms was filtered out and then Sample No. 2 was added at a ratio of 1.5:0.5 | 72 | 35 |
| 3/4 | Sample from Sampling Point 1 | 72 | 35 |
| 1/5 | Seawater from point of input water to the seawater desalination facility in Palmahim, Israel | 72 | 35 |
| 2/5 | Seawater from point of input water to the seawater desalination facility in Palmahim, Israel | 72 | 35 |
| 3/5 | Sample from Sampling Point 2 | 72 | 35 |

Results
Microorganism's Growth in Incubator Conditions:

The change in medium color was visually detected. Images obtained using a camera (PowerShot A95, Canon) were scanned using a Perfection 10 scanner (Espon, Japan), at a scanning resolution of 300 dpi.

The results of the first control Petri dish (with the sterile distilled water) showed that there was no change in the medium color, whereas, in the second Petri dish (with water from sample point 1), metabolic activity of the microorganisms took place, which caused a significant (visible) change in the medium color, i.e. the appearance of a strong violet color.

Examining the Color Changes with Various Samples and Conditions:

In the following validation experiments, various solutions (as indicated in Table 4) were allowed to circulate on the surface of the biosensor in order to examine the color indicator reaction in various situations, including extreme situations of the circulating solutions: sterile solutions with no microorganisms, solutions with no nutrients which contain microorganisms, solutions which contain nutrients but do not contain microorganisms, and solutions of Shafdan water. In addition, different temperatures were tested.

The results obtained for the different experiments are shown in Table 5.

TABLE 5 appearance of the biosensor signal in different experiments.

| Batch No. | Tested sample | Hours[1] | T (° C.) | Color[2] |
|---|---|---|---|---|
| Control | Sterile saline | 96 | 35 | − |
| 1/1 | Saline containing extracted microorganisms | 72 | 35 | − |
| 2/1 | Sample from Sampling Point 1 however diluted 1:1 with sterile saline | 48 | 35 | + |
| 3/1 | Sample from Sampling Point 1 | 24, 72 | 35 | +, + |
| 1/2 | Sample from Sampling Point No. 1 mixed with 50 ml 1.8% Nutrient Broth | 24, 96 | 35 | +, + |
| 2/2 | Sample from Sampling Point 1 | 96 | 35 | + |
| 3/2 | Sample from Sampling Point 1 | 24, 96 | 24 | −, + |

TABLE 5-continued appearance of the biosensor signal in different experiments.

| Batch No. | Tested sample | Hours[1] | T (° C.) | Color[2] |
|---|---|---|---|---|
| 1/3 | saline containing extracted microorganisms | 48 | 35 | − |
| 2/3 | Sample from Sampling Point No. 1, from which any existing microorganisms was filtered out | 48 | 35 | − |
| 3/3 | Sample from Sampling Point 1 | 48 | 35 | + |
| 1/4 | Sample from Sampling Point No. 1 mixed with 15 ml 1.8% Nutrient Broth | 48 | 35 | + |
| 2/4 | Sample from Sampling Point No. 1, from which any existing microorganisms was filtered out and to which saline with extracted microorganism was added at a ratio of 1.5:0.5 | 48 | 35 | + |
| 3/4 | Sample from Sampling Point 1 | 72 | 35 | + |
| 1/5 | Seawater from point of input water to the seawater desalination facility in Palmahim, Israel | 72 | 35 | + |
| 2/5 | Seawater from point of input water to the seawater desalination facility in Palmahim, Israel | 72 | 35 | + |

[1]time of image acquisition from the circulating system
[2](+) indicating appearance of violet color, (−) indicating no color change The results of the above experiment show that the violet color appeared on the surface of the biosensor only when there was a combination of microorganisms and nutrients. If one of these elements was missing from the circulation solution, the color remained as original. In addition, the longer the duration of circulation, the greater the intensity and surface coverage of the violet color was on the surface of the biosensor.

Thus, the results of the experiment show that there was a linear dependency between the quantity of microorganisms growing on the surface of the biosensor and the quantity and intensity of violet color which appeared on the biosensing medium. In all experiments, the violet color, if appeared on the surface of the biosensor, was uniform. Furthermore, after four days of circulation, the color was not washed off the biosensing medium into the circulating fluid.

The last batch experiment (Batch 5), which involved circulation of seawater, which is used for input to the seawater desalination facility, showed that the color appeared with this type of water as well—albeit only after a circulation time longer than 72 hours. The longtime required for the appearance of the violet color may be explained by the low TOC of seawater. These results show that it will be possible to use the biosensor for various types of fluids.

Example 2

Biofouling Indexing and Studies

The purpose of these experiments was to define a Biofouling Index and the use thereof to determine the correlation between the color/intensity on the biosensor in line with the biofouling Index and the amount of biofilm grown on the surface of the RO membranes, using different sources of water.

To this end, three input solutions, Sampling Points No. 3, 4 and 5, as defined in Table 3 were circulated, either in the biosensing chamber for 24 hours, or through RO miniature membranes at the Shafdan facility for 15 days, and the actual growth of biofilm from these solutions on the surface of the RO membranes as compared to the growth on the biosensor were measured.
Biofouling Growth on the Biosensor:

The change in color on the biosensor was determined for each water sample in six repetitions as described above.

Circulation conditions: circulation flow: 90 ml/min; circulation container volume: 2 L; duration of circulation: 24 hours, temperature of 35° C.
Biofouling Growth on RO Membranes:

Biofilm was allowed to grow on the surface of miniature RO membranes (ESNA1-LF, Hydranautics, USA), equipped within a device having the membrane held within a closed chamber, the chamber comprising a feed inlet, brine outlet and permeate outlet for fluids, where the pressure obtain from the desalination pilot pressurized flows.

The surface area of the membrane was 33.44 cm$^2$ (38×88 mm) For each water sample, three repetitions were preformed.

During the experiment, parameters such as pressures, water flows, conductivity, temperature and pH were recorded in order to monitor and record possible changes in the membrane output as a result of the growth of biofilm.

After completion of the circulation experiments (15 days circulation), the membranes were removed from the chamber and stored in a sterilized saline solution at a temperature of 4° C.

For biofilm analysis a 5×5 mm membrane segment was taken from each of the tested membranes. Each segment was inserted into an Eppendorf test tube comprising 2 ml 0.24% sterilized TRIS solution (pH 7.2) and the test tubes were turned upside down gently several time.

Then, rinsing of the membrane took place by replacing, three times, a portion of the solution (1 ml) with a new volume of TRIS solution (1 ml). Between each portion replacement, the test tube was turned upside down gently several times.

The rinsed membranes were then stained with SYTO based dye (Molecular Probes, USA, preparation described below) which was used to stain the microorganism and with Tetramethylrhodamine (Molecular Probes, USA, preparation described below) which was used to stain the extracellular polymeric surface (EPS) of the organisms and thus used as a marker for biovolume formation.

Table 6 shows the color shades and the wavelengths of these stains under excitation and emission.

TABLE 6

Dye type for cells and EPS coloring

| Dye type | Color | Excitation | Emission |
|---|---|---|---|
| SYTO9 | Green | DNA: 485 | DNA: 498 |
| | | RNA: 486 | RNA: 501 |
| Tetramethylrhodamine (C-860) | Red | 555 | 580 |

For the staining, the commercial SYTO dye was diluted with TRIS-HCl to a concentration of 0.3% (v/v) and was kept in aliquots of 70 μl in Eppendorf test tube, at −20° C. until further use.

The commercial Tetramethylrhodamine dye was dissolved in 5 ml of 0.1 M sodium bicarbonate (NaHCO$_3$) to obtain a concentration of 2 mg/ml. This stock solution was kept at −20° C. until further use.

For staining, the stock solution of Tetramethylrhodamine was diluted with 0.24% TRIS-HCl to obtain a concentration of 0.2 mg/ml. The diluted solutions were kept in small aliquots of 70 µl at −20° C.

The rinsed segments of membrane were placed in a large Petri dish and 35 µl of SYTO9 was added onto the membrane segments, to allow a uniform distribution. The Petri dish was closed and covered with aluminum foil to keep a dark environment for 25 minutes.

After 25 minutes, each stained membrane segment was inserted into an Eppendorf test tube comprising 2 ml 0.24% sterilized TRIS solution (pH 7.2) and the test tubes were turned upside down gently several time.

Then, rinsing of the membrane took place by replacing, three times, a portion of the solution (1 ml) with a new volume of TRIS solution (1 ml). Between each portion replacement, the test tube was turned upside down gently several times.

After the rinsing, the segments were placed in a large Petri dish and 35 µl of Tetramethylrhodamine was added onto the membrane, to allow a uniform distribution. The Petri dish was closed and covered with aluminum foil to keep a dark environment for 25 minutes.

After 25 minutes, the stained membrane segments were rinsed as described before.

The rinsed membrane segments, stained with the two dye materials, were placed in a large Petri dish and 50 µl of TRIS solution was added onto the membranes.

Prior to microscope analysis, a drop of immersion oil was added onto the cover glass.

Examination of the membranes was performed using a confocal laser scanning microscopy (CLSM) (Leica, Microsystems Germany), whereas STOY9 and Tetramethylrhodamine were excited at wavelength of 488 nm and 532 nm, respectively.

Results:

Biofouling Index:

The results of the three measured solutions, from Sampling Points 3, 4 and 5, were used to obtain a biofouling index.

Characterization of the feed water before the circulation experiments:

Sampling Point 3/Feed 1: amount of microorganisms: colony-forming unit (CFU)/ml—588; total organic carbon (TOC)—14.2 mg/l; conductivity: 1,620 µmho; pH=6.7; biological oxygen demand (BOD)=6 mg/l Sampling Point 4/Feed II: amount of microorganisms: colony-forming unit (CFU)/ml—18,000; total organic carbon (TOC)—39 mg/l; conductivity: 4,005 µmho; pH=7.19; biological oxygen demand (BOD)=25 mg/l Sampling Point 5/Feed III: amount of microorganisms: colony-forming unit (CFU)/ml—48,000; total organic carbon (TOC)—68.5 mg/l; conductivity: 6,740 µmho; pH=7.42; biological oxygen demand (BOD)=103 mg/l.

Analysis of the color intensity of each tested sample from the three Sampling Points (referred to as Feed I, II and III) was quantified and indexed as a Biofouling Index.

The biofouling Index was determined as follows:

Biofouling Index=100×PPP×(1−PPP)+(100−LL)×PPP where:

Biofouling Index—a numerical value which defines the biofouling level

PPP (Purple Pixels Percentage)—the percentage of the pixels which are purple (decimal fraction)

LL (Lightness Level)—the intensity

Figure 2:
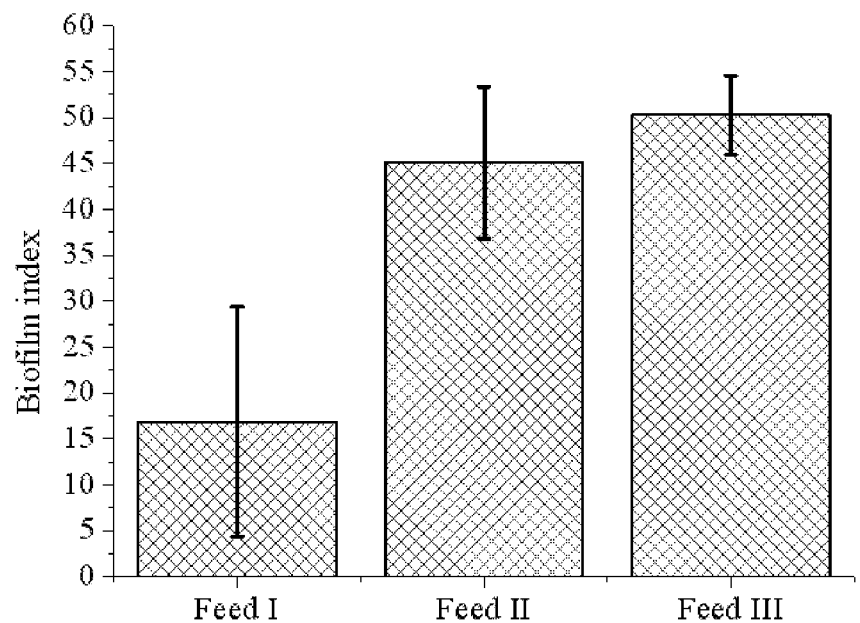
FIG. 2 provides a graph showing a biofilm index for the three different water feeds (to stage I, to stage II and to stage III in reverse osmosis desalination system), determined using a biosensor according to an embodiment of the invention.

FIG. 2 shows the intensity color (average of each 6 repetitions) with the different water.

For simplicity, the Biofouling Index was translated into a biofouling score, A, B, C, . . . F, according to ranges of biofouling, with lower biofouling range, representing low biofouling identified as score A. The correlating score is identified in Table 7.

TABLE 7

Biofilm prediction based on the Biofouling Index

| Description | Biofouling Index | Biofouling level |
| --- | --- | --- |
| Clean Water | biofouling index <0.0002 | A |
| Minor Biofouling | biofouling index <6 | B |
| Moderate Biofouling | biofouling index <40 | C |
| Moderate-severe Biofouling | biofouling index <48 | D |
| Severe Biofouling | biofouling index <70 | E |
| Extremely Severe Biofouling | biofouling index >=70 | F |

Biofouling on RO Membranes

Fluid samples from the Sampling Points were also used to determine biofouling on RO membranes.

Figure 3:
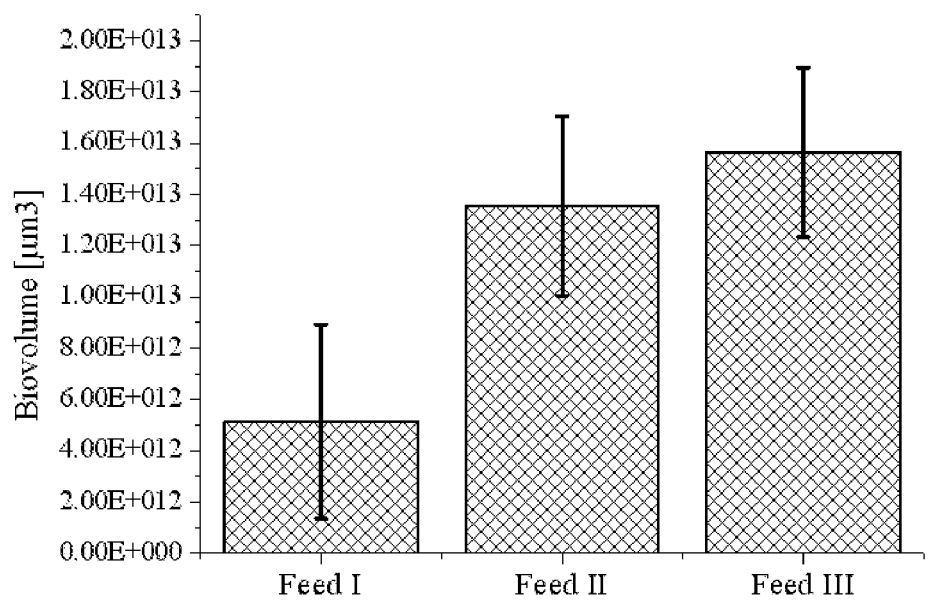
FIG. 3 provides a graph showing of the biovolume (in μm³) of biofilm grown on a reverse osmosis (RO) membrane after 15 days, for three different feed water stages, to stage I, to stage II and to stage III, the biovolume being measured with a confocal laser scanning microscopy (CLSM).

The staining of the RO membranes with SYTO9 and Tetramethylrhodamine, provided information about the presence and quantity of microorganisms and the extracellular polymeric substance (EPS), respectively. The CLSM images were scanned and analyzed with PHLIP software (http://sourceforge.net/projects/phlip/) which enabled quantization of CLSM data with respect to the biovolume of the biofilm. FIG. 3 provides the biovolume obtained for each fluid, Feed I, Feed II and Feed III.

Reliability of the Biosensor Results

Applying a statistical t-test on the results of the biofilm index obtained after 24 hours of water circulation (FIG. 2) which led to the determination of the Biofouling Index (Table 7) and the biovolume (FIG. 3) of biofilm which developed on the RO membrane after 15 days of water circulation indicated a significant positive correlation of more than 0.9.

Example 3

Finding the Minimal Conditions for the Biosensor Reaction

Samples from Sampling Point No. 2 (SP2) were diluted with saline (to obtain three diluted solutions, Table 8) in order to determine the sensitivity of the biosensor, namely, the minimal detectable TOC and microorganism concentration. In all tested samples, the pH was 7.3 and the BOD was <5 mg/l.

TABLE 8

Tested samples

| No. | Tested Sample | CFU (CFU/ml) | TOC (mg/l) | C* (µmho) |
| --- | --- | --- | --- | --- |
| 1 | 1 L SP2 + 1 L saline | 195 | 6.2 | 1,470 |
| 2 | 0.667 L SP2 + 1.333 L saline | 130 | 4.4 | 1,467 |
| 3 | 0.400 L SP2 + 1.6 L Saline | 78 | 3.1 | 1,464 |

*Conductivity

The following conditions were applied: circulation flow: 90 ml/min, circulation volume of 2 L; duration of circulation 24 h at a temperature of 35° C.

Results:

After 24 hours of circulation in the biosensor apparatus, the intensity of color (purple) appearing on the biosensor was determined and ranked using the biofouling index at a level B. The results thus led to the conclusion that the biosensor of the invention is able to detect biofouling at low level of microorganisms, i.e. at a low TOC of about 3 mg/l and at a low microorganism's count of 78 CFU/ml.

Example 4

Application of the Biosensor

The objective of this example was to determine the minimum amount of hypochlorite (disinfectant) required for preventing biofouling.

The source of the tested water (the Shafdan) contains ammonia ($NH_3$) at values which vary between approximately 2-10 mg/L. When sodium hypochlorite (NaOCl) is added, chloramines are formed, e.g. $NCl_3$, $NHCl_2$, $NH_2Cl$, which are used to prevent biofouling. Residual chlorine damages the RO membrane. Thus, it is very important to use a minimal amount of sodium hypochlorite to prevent, on the one hand biofouling, and prevent, on the other hand, damage to the RO membrane.

Methods:

Hypochlorite was dissolved to obtain a stock solution of 140 mg/L. Dilutions of this stock solution were as detailed in Table 9. The dilutions were injected into the water circulating in the biosensing apparatus and the total chlorine concentration was measured for each dilution. As control, no hypochlorite was added.

Circulation conditions: flow: 90 ml/min; circulation container volume: 2 L; duration of circulation: 24 hours at a temperature of 35° C.

In addition, water from sampling Point No. 3 (SP3) was allowed to flow through miniature membrane facilities (as described above) in parallel, for 15 days in order to allow growth of biofilm on the surface of the membranes. After 15 days, the membranes were treated and analyzed as described above in order to determine the resulting biovolume.

Results

The total chloramines and the biofouling index in the tested sample, after 24 h circulation are provided in Table 9. The biofouling index as a function of total chlorine is provided in FIG. 4.

TABLE 9 chlorine concentration and biofouling index

| Sodium hypochlorite [mg/l] | Total Chloramines [mg/l] | Biofouling index |
|---|---|---|
| Control | | C |
| 0.7 | 0.17 | B |
| 1.4 | 0.29 | B |
| 2.1 | 0.45 | B |
| 2.8 | 0.94 | B |
| 2.8 | 1.0 | B |
| 4.2 | 1.42 | B |
| 4.2 | 1.48 | B |
| 4.6 | 1.63 | B |
| 5.6 | 1.86 | B |

Figure 4:
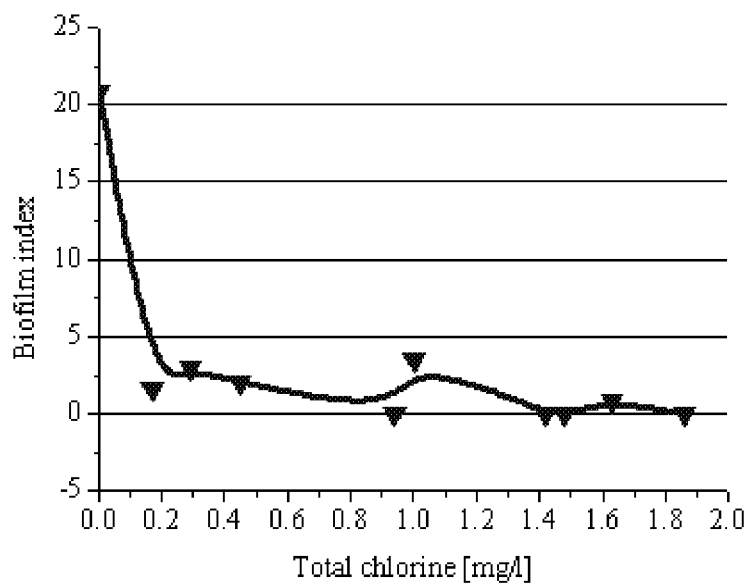
FIG. 4 provides a graph showing a biofouling index as a function of total chlorine concentration in water.

The addition of hypochlorite exhibited a drop in the biofouling index (from C to B). A lowest biofouling index was obtained for a total chlorine concentration of 1.4 and more [mg/L], at which biofouling index was close to zero (FIG. 4). Thus, for a close to zero biofouling, a 4.2 mg/l amount of hypochlorite would be sufficient to prevent biofouling, without creating harmful chlorine entities.

Growing Biofilm on RO Membranes with Input Water Containing Chloramines

On the basis of the previous results, it was decided to use total chloramines concentration of 1.5 mg/L obtained by injection of 4.2 mg/L hypochlorite. The duration of injection of hypochlorite into the Stage I (SP1) input water was 4 hours per day, every day.

After 15 days the membranes were disassembled and examined under CLSM microscopy. A total of four membranes were examined, two used as control (no hypochlorite added). The data processing was performed in a similar manner as detailed above.

Figure 5:
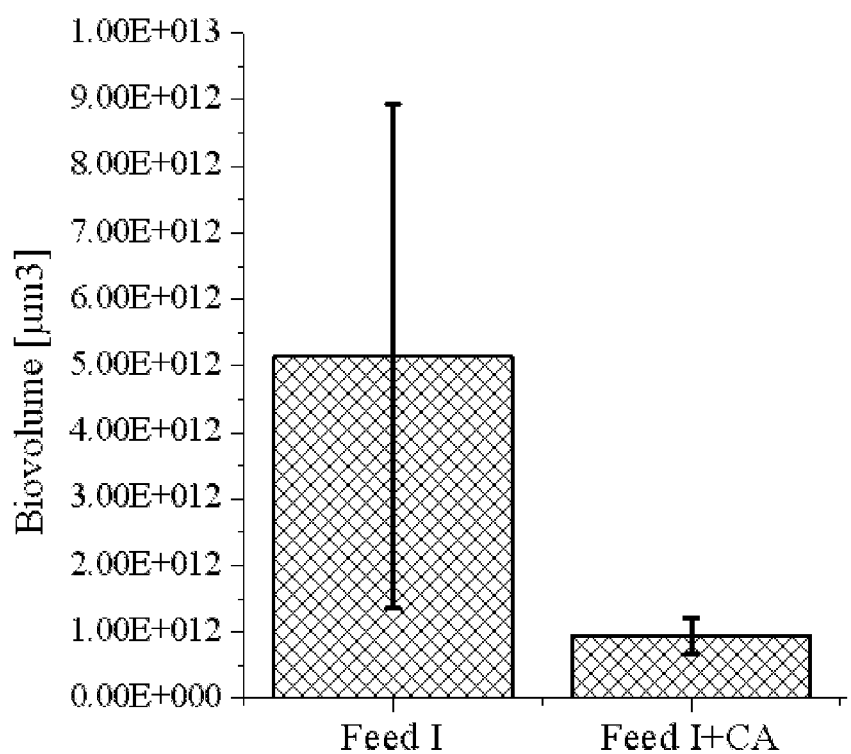
FIG. 5 provides a graph showing biovolume of biofilm grown on RO membrane for feed water to stage I (Feed I) without chloramines, and for feed water to stage I with chloramines (Feed I+CA) after 15 days, measured with CLSM.

FIG. 5 shows the biovolume of the biofilm developed on each membrane when hypochlorite was injected into the input water in order to produce chloramines at the concentration recommended by the prediction instrument: 1.5 mg/L, by comparison to the biofilm which developed on the membranes in the same input water without hypochlorite. The results were calculated as an average of 18 scanned and calculated points.

The results presented in FIG. 5 show that creating a low dose of 1.5 mg/L of chloramines, obtained by addition of 4.2 mg/L hypochlorite, prevented the development of biofilm on the membrane; the biovolume was about ⅕ the biofilm volume developed on the membrane under the same circulation conditions without the addition of hypochlorite.

Figure 6:
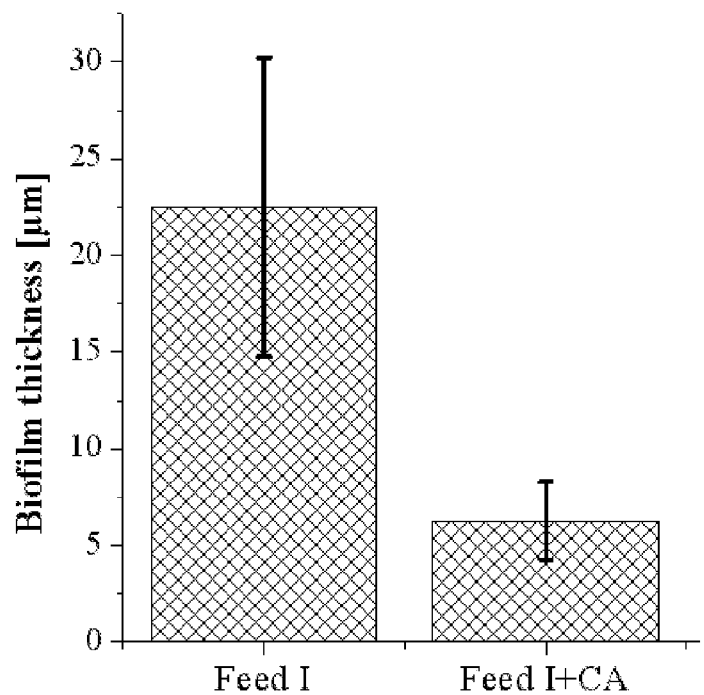
FIG. 6 provides a graph showing thickness of biofilm grown on RO membrane with feed water to stage I (Feed I) and feed water to stage I with chloramines (Feed I+CA) after 15 days, measured with CLSM.

FIG. 6 provides the biofilm thickness, showing that the thickness of the biofilm after 15 days in the presence of chloramines (i.e. when hypochlorite was added) was about ⅕ the thickness of the biofilm developed in the absence of chloramines.

Figure 7:
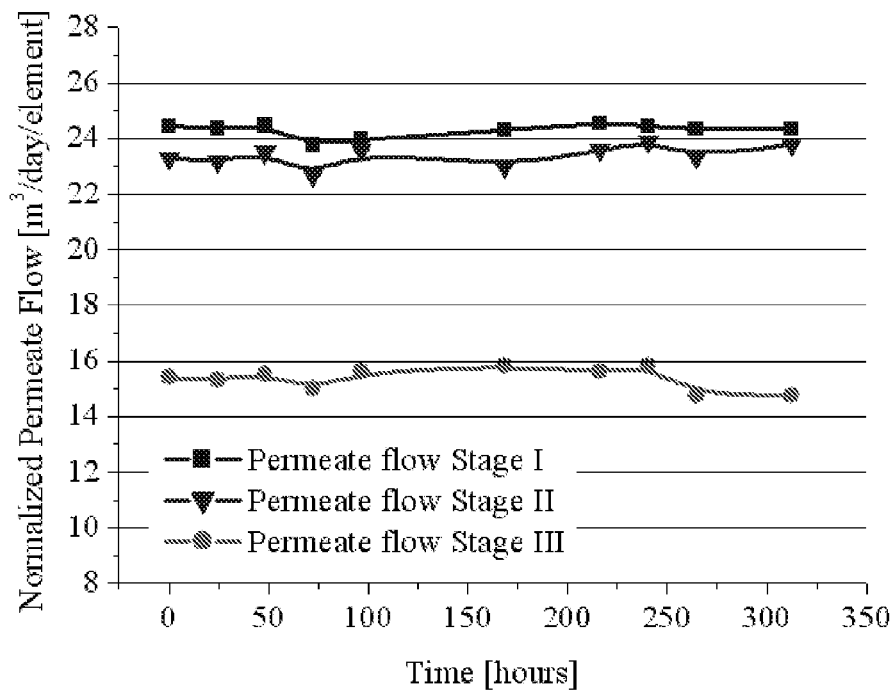
FIG. 7 provides a graph showing the normalized permeate flow as a function of operation time for a pilot plant with low dose of chloramines as determined with the bio-sensor test.

Also examined was the effect of preventing the development of biofilm on the membrane surface when 4.2 mg/L hypochlorite were added. It has been found that normalized flow for 320 hours, showed no affect, and in particular no decrease in permeate flow, neither in Stage I nor in Stage II and Stage III (FIG. 7). It was also found that treatment with hypochlorite reduced biofouling on the membranes (data not shown).

The invention claimed is:

1. A biosensor, comprising:
    (a) a scaffold comprising a matrix formed from a scaffold forming material that turns from solid to liquid at a temperature above 35° C., and not more than 95° C. and into a solid or semi solid structure upon cooling; and
    (b) a dye complex comprising a clay mineral bound to a dye material, wherein the dye material provides a detectable signal in the presence of microorganisms, wherein the dye complex is embedded in the scaffold.

2. The biosensor of claim 1, wherein the dye complex is at least partially embedded in pores of the scaffold.

3. The biosensor of claim 1, further comprising an alkanol.

4. The biosensor of claim 1, wherein the dye complex has a molecular weight in the range of 300 g/mole to 1500 g/mole.

5. The biosensor of claim 1, wherein embedment of the dye complex comprises physical entrapment of the complex in pores of the scaffold, such that at least part of the dye material remains exposed out of the scaffold.

6. The biosensor of claim 1, wherein the scaffold forming material comprises a polymeric material.

7. The biosensor of claim 6, wherein the polymeric material is selected from the group consisting of a polysaccharide, silicon-based polymers, polytetrafluoroethylene, polyethelene, polypropylene, polyethyleneterephthalate, polyurethane, polystyrene, polysulfone, polyester, polyhydroxyacids, polycarbonate, polyimide, and polyamide.

8. The biosensor of claim 7, wherein the polysaccharide is agar.

9. The biosensor of claim 1, wherein the dye material belongs to the family of tetrazolium compounds.

10. The biosensor of claim 9, wherein the tetrazolium compound is 2,5-diphenyl-3-[alpha-naphthyl]-1-tetrazolium chloride.

11. The biosensor of claim 1, wherein the clay mineral is selected from the group consisting of Kaolin, Smectite, Illitem Chlorite, Sepiolite and Attapulgite.

12. The biosensor of claim 11, wherein the clay mineral is Kaolin.

13. A biosensor, comprising:
   (a) a scaffold comprising a matrix comprising a scaffold forming material having a phase transition temperature from solid to liquid between 35° C. and 95° C.; and
   (b) a dye complex comprising a day mineral bound to a dye material being selected from the group consisting of a chromophore and fluorophore,
   wherein the dye complex is embedded in the scaffold.

14. The biosensor of claim 13, wherein the dye complex is at least partially embedded in pores of the scaffold.

15. The biosensor of claim 13, wherein the dye material belongs to the family of tetrazolium compounds.

16. The biosensor of claim 13, wherein the tetrazolium compound is 2,5-diphenyl-3-[alpha-naphthyl]-1-tetrazolium chloride.

17. The biosensor of claim 13, wherein embedment of the dye complex comprises physical entrapment of the complex in pores of the scaffold, such that at least part of the dye material remains exposed out of the scaffold.

18. A process for the preparation of a biosensor, the method comprises:
   (a) mixing a dye complex comprising a clay mineral bound to a dye material that provides a detectable signal in the presence of microorganisms with a scaffold-forming material that turns from solid to liquid at a temperature above 35° C. and not more than 95° C. and into a solid or semi solid structure upon cooling, said mixing is, at a temperature at which the dye complex and the scaffold forming material are in an aqueous fluid mixture;
   (b) adding to the fluid mixture a non-electrolytic reagent; and
   (c) cooling the fluid mixture with the non-electrolytic reagent to a temperature at which the mixture turns into a solid or semi-solid;
   whereby a biosensor is formed comprising a scaffold and the dye complex being embedded in the scaffold.

19. The process of claim 18, wherein the mixing between the dye material and the clay mineral is at a pH in the range of 4 to 6.

20. The process of claim 18, wherein the clay mineral is selected from the group consisting of Kaolin, Smectite, Illitem Chlorite, Sepiolite and Attapulgite; the dye material is selected from tetrazolium compounds; and the scaffold forming material is selected from the group consisting of a polysaccharide, silicon-based polymers, polytetrafluoroethylene, polyethelene, polypropylene, polyethyleneterephthalate, polyurethane, polystyrene, polysulfone, polyester, polyhydroxyacids, polycarbonate, polyimide, and polyamide.

21. The process of claim 18, wherein the dye complex and the scaffold-forming material are mixed at a temperature in the range of from 35° C. to 95° C.

22. The process of claim 18, wherein mixture of the scaffold-forming material and the dye complex is at a stoichometric ratio of 4:1.

* * * * *